United States Patent
Heinz et al.

(10) Patent No.: US 7,582,102 B2
(45) Date of Patent: Sep. 1, 2009

(54) MECHANICAL ADVANTAGE TOURNIQUET

(75) Inventors: Thomas J. Heinz, La Canada, CA (US);
Royce Rumsey, Laguna Beach, CA (US); Ed Bannister, Victorville, CA (US); Sai Chung Chan, Irvine, CA (US)

(73) Assignee: Pyng Medical Corp., Richmond (CA)

( * ) Notice: Subject to any disclaimer, the term of this patent is extended or adjusted under 35 U.S.C. 154(b) by 392 days.

(21) Appl. No.: 10/961,401

(22) Filed: Oct. 12, 2004

(65) Prior Publication Data
US 2005/0113866 A1 May 26, 2005

Related U.S. Application Data

(60) Provisional application No. 60/509,917, filed on Oct. 10, 2003, provisional application No. 60/615,027, filed on Oct. 4, 2004.

(51) Int. Cl.
*A61B 17/00* (2006.01)

(52) U.S. Cl. .................................... 606/203
(58) Field of Classification Search ............ 606/201, 606/202, 203; 24/269, 483, 909
See application file for complete search history.

(56) References Cited

U.S. PATENT DOCUMENTS

| | | | | | |
|---|---|---|---|---|---|
| 2,553,390 | A | * | 5/1951 | Streyckmans | ............... 24/68 D |
| 2,660,174 | A | * | 11/1953 | Saemann | ..................... 606/202 |
| 2,903,172 | A | * | 9/1959 | Carter | ......................... 224/219 |
| 3,142,880 | A | * | 8/1964 | Davies | ..................... 24/265 C |
| 3,570,495 | A | * | 3/1971 | Wright | ....................... 606/202 |
| 4,526,165 | A | * | 7/1985 | Mielnik et al. | ............... 128/882 |
| 5,628,723 | A | * | 5/1997 | Grau | ............................ 602/53 |
| 5,661,876 | A | * | 9/1997 | Goldenberg | ................... 24/19 |
| 6,213,968 | B1 | * | 4/2001 | Heinz et al. | ................... 602/19 |
| 6,960,223 | B1 | * | 11/2005 | Ambach | ...................... 606/203 |
| 2003/0139766 | A1 | * | 7/2003 | McEwen et al. | ............ 606/203 |

* cited by examiner

*Primary Examiner*—Todd E Manahan
*Assistant Examiner*—Kevin Everage
(74) *Attorney, Agent, or Firm*—Pequignot + Myers LLC

(57) ABSTRACT

A pressure control apparatus for restricting a flow of blood through or from a body part includes at least one arcuate member for attaching to the body part. The at least one arcuate member has a first end and an opposite second end. The first end includes a hook for fastening to a buckle mounted at the opposite second end. A mechanical advantage power system includes a turnkey and is connected to the at least one arcuate member and serves to adjusting a pressure of the apparatus on the body part by turning the turnkey. An elongated strap is disposed on at least a circumferential portion of the arcuate member for circumferentially tightening the apparatus around the body part. A locking device closes the apparatus around the body part and is attached to the at least one arcuate member. A cover or shroud is disposed on an outer perimeter of the at least one arcuate member for enclosing a portion of the mechanical advantage power system.

31 Claims, 11 Drawing Sheets

MECHANICAL ADVANTAGE TOURNIQUET

This application claims priority to applicants' copending U.S. Provisional Application Ser. No. 60/509,917 entitled "MECHANICAL ADVANTAGE TOURNIQUET" filed Oct. 10, 2003, and U.S. Provisional Application No. 60/615,027 entitled "MECHANICAL ADVANTAGE TOURNIQUET III (C-CLAMP VERSION)" filed Oct. 4, 2004. The entirety of these patent applications is incorporated herein by reference.

BACKGROUND OF THE INVENTION

1. Field of the Invention

The present invention relates to a tourniquet with an improved tightening system that provides a mechanical advantage for applying a compression force to an appendage.

2. Description of the Related Art

A tourniquet is a device for temporarily controlling the flow of blood through or from a large artery in an appendage under emergency conditions as the tourniquet cuts off the blood supply to the appendage for a period of time. Although primarily used as a first-aid or triage measure, tourniquets can also be used in a medical facility during surgical procedures.

To be effective, a tourniquet must be tight enough to stop the arterial blood flow to the appendage. However, a tourniquet is often applied as an emergency measure by individuals with knowledge that a tourniquet must be used, yet without experience in the level of medical care to properly apply the tourniquet and effectively restrict the flow of blood. In many emergency situations, tourniquets are an improvised form of treatment taking the form of a cloth rag being tied to the injured appendage. The state of mind in which individuals applying and/or receiving the tourniquet may find themselves include shock, anxiety and desperation. Further, environmental conditions, such as the rain, snow, sandstorm, or dust storm also affect the efficiency with which a tourniquet can be applied to an injured appendage.

SUMMARY OF THE INVENTION

The present invention relates to a new type of tourniquet for use in emergency medicine, either in the field or at a medical facility. The present invention stops or restricts the flow of blood between the heart and an injured appendage by applying sustained pressure to the appendage between the heart and the injury. One embodiment of the present invention takes into consideration that a user of the invention may be, for example, a hiker or backpacker, mountain climber, merchant seaman, vehicular or industrial accident or natural disaster victim, or a soldier in the battlefield, and the unique environmental circumstances and physical impediments that these individuals may face when injured or wounded.

Using the soldier as an example, the mechanical advantage tourniquet is designed for a fast and easy application as required by the soldier under tremendous pressure and/or in shock, and the need to quickly apply and tighten a tourniquet on his own body, with possibly one hand, in approximately five seconds. As such, the device is a continuous strap, and not pre-looped to allow use in the field by a soldier whose leg or legs may be trapped or obstructed. The bionics of the mechanical advantage tourniquet of the present invention, can more efficiently and effectively compress an injured appendage, thereby temporarily stopping the flow of blood.

The tourniquet of the present invention is lightweight and portable so that it can be carried in a pocket of a soldier's uniform and is designed so that a weak and/or wounded soldier can apply it in the field or under combat conditions. For example, the soldier can apply the tourniquet while wearing gloves and the tourniquet is effective over rain and snow gear. Further the tourniquet can have luminescent markings to make it easy to use in at night or in a darkened environment. The tourniquet is also self-contained with no additional pieces or assembly required. Further, the tourniquet can be easily and successfully applied to the body under adverse weather conditions, such as in extreme temperatures ranging from at least +40 degrees to 125 degrees F., in and around ice, snow, rain, mud, saltwater, blowing sand and dirt, and other environmental obstacles. The tourniquet can also withstand all standard consumer product impact tests.

The present invention includes a tourniquet or pressure control apparatus for restricting a flow of blood through or from a body part, the apparatus including at least one arcuate member which can be a base member or a C-clip, for example, for attaching to the body part. The arcuate member has a first end and an opposite second end. A primary tightening device including a mechanical advantage power system can be mounted on the at least one arcuate member for adjusting a pressure of the apparatus on the body part. A secondary tightening device or cinch strap can be disposed on at least a portion of the arcuate member for circumferentially tightening the apparatus on the body part. A locking device can securely close the apparatus around the body part by being attached to the arcuate member.

The primary tightening device includes a mechanical advantage power system that can multiply an output force while minimizing the input force needed to create the output force. Such mechanical advantage power systems include, but are not limited to pulleys, eyelets, post systems, needle bobbins, gears, levers, wheels, and cams.

The present invention also includes a method of restricting the flow of blood through or from a body part with a pressure control apparatus. The apparatus has at least one arcuate member that can be mounted on or attached to the body part. The one arcuate member has a rear end portion and a front end portion so that a primary tightening device can be mounted on the front end portion and a secondary tightening device can be mounted on the rear end portion. The primary tightening device adjusts a pressure of the apparatus on the body part. The secondary tightening device circumferentially tightens the apparatus on the body part. A locking device closes the apparatus around the body part, and is attached to the arcuate member. The method includes placing the arcuate member and the secondary tightening device around the body part to be treated; threading the secondary tightening device through the locking device, and over a second end of the at least one arcuate member or engagement of a pre-threaded tightening device with the second end of the at least one arcuate member to allow for one-handed application; setting the locking device to clasp the external ends of the second end of the at least one arcuate member; pulling the secondary tightening device in a direction tangent to the at least one arcuate member until the secondary tightening device is secured tightly to the body part; raising the turnkey from a horizontal position to a vertical position; turning the turnkey in a predetermined direction until the primary tightening device can no longer be turned; and folding the turnkey to a horizontal position.

The present invention further includes a pressure control apparatus for restricting a flow of blood through or from a body part having mounting means for mounting the pressure control apparatus on the body part to be treated. Tightening means are attached to the mounting means for tightening the pressure control apparatus onto the body part to be treated.

Locking means are operatively connected to the tightening means for locking the pressure control apparatus onto the body part to be treated.

BRIEF DESCRIPTION OF THE DRAWINGS

The features of the invention will be more readily understood with reference to the following description and the attached drawings, wherein.

DETAILED DESCRIPTION OF INVENTION

Figure 1:
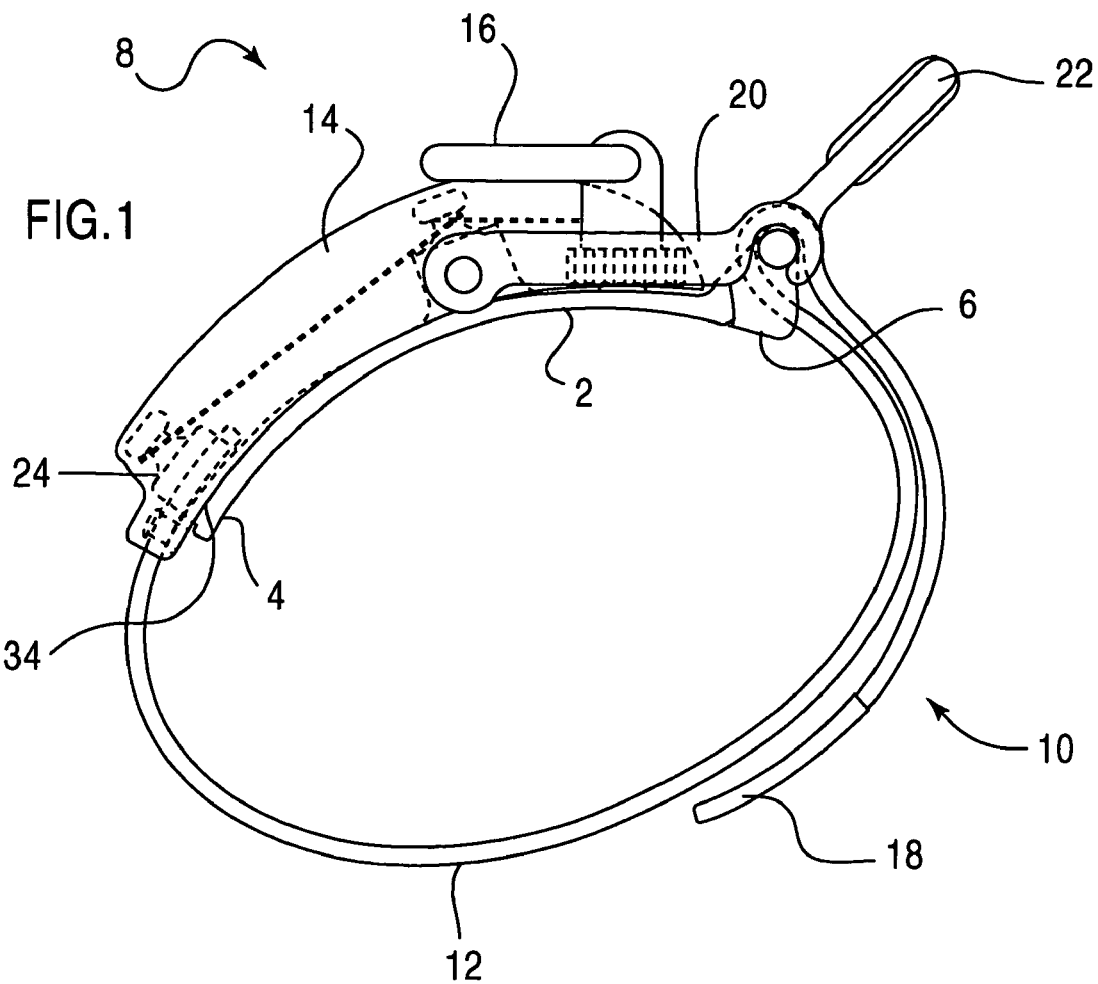
FIG. 1 illustrates a side view of the tourniquet according to a first embodiment of the present invention.

FIG. 1 illustrates a side view of the mechanical advantage tourniquet 10 according to a first embodiment of the present invention. As shown in FIG. 1, the tourniquet 10 includes a mechanical advantage power system 8, an arcuate member or base 2, a strap 12, and a locking member 20.

The base 2 has a first end 4 and a second end 6, and serves as a mounting means for mounting the tourniquet 10 onto the injured appendage. The base 2 can be formed from a flexible material, including but not limited to, a polymeric material such as acetal or nylon.

The strap 12, such as a cinch strap is an elongated member that can also be formed from any suitably flexible material including, but not limited to, nylon. The strap 12 extends from the first end 4 of the base 2 around the injured appendage where it is threaded through and locked into place by the locking member 20. In combination, the strap 12, along with the mechanical advantage power system 8, serve as tightening means for tightening the tourniquet on the injured appendage.

Figure 2:
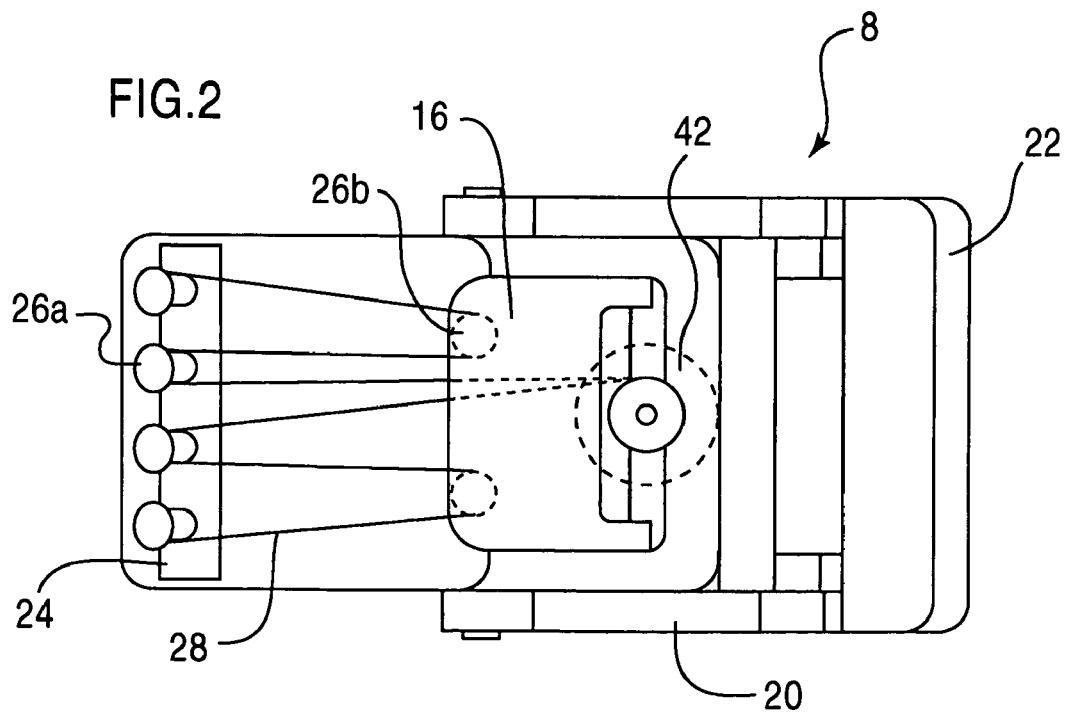
FIG. 2 illustrates a top view of the tourniquet mechanical advantage power system according to a first embodiment of the present invention.

FIG. 1 illustrates the mechanical advantage power system 8, which is a device that can multiply an output force while reducing an input force needed to create the output force. Thus, the mechanical advantage power system 8 allows any size user to simply and easily adjust and tighten the tourniquet 10 onto the appendage with minimum effort. The power system 8 creates a mechanical advantage-assisted tension that cuts off the blood supply to an appendage once the strap 12 encircling the appendage has been pulled tight and locked into place by the locking member 20. As shown in FIG. 1, the mechanical advantage power system 8 is mounted onto the base 2 between the first end 4 and the second end 6 of the base. The power system 8 includes components designed to apply a controlled pressure to the injured appendage, and thereby restrict the flow of blood through or from the injury on the appendage. The components include a graduated track 34 integrally formed on an outer surface of the base 2, at least one platen 24 disposed on the track 34 at the first end 4 having a plurality of posts 26a, 26b; a winding cord 28; a winch or cord retracting device 42; and a turnkey 16. The winch 42 is disposed on a second end 6 of the base 2, and the turnkey 16, shown in a folded down locked position in FIGS. 1 and 2, is pivotally mounted onto the winch 42 to rotate the winch. The graduated track 34 allows the platen 24 of the base 2, to slide along the perimeter of the base 2.

The platen 24 can be formed from any polymeric material, including but not limited to acetal and nylon. The platen 24 secures one end of the strap 12 at the first end 4 of the base 2. A first set of linearly arranged posts 26a project from the platen 24 to anchor a braided or interwoven winding cord 28. A second set of posts that may be directly mounted onto the base 2 or project from a second platen 24, provide a guide for the cord 28. The winding cord 28 is wound around the posts 26a, 26b and the winch 42, and threaded through an opening in the winch 42 in a serpentine manner, as shown on FIG. 2. Turning the turnkey 16 rotates the winch 42 causing the cord 28 to wrap around the winch, and pulls the cord 28 into tension between the platen 24 and the winch 42, thereby providing a mechanical advantage for tightening the tourniquet on the appendage.

The turnkey 16 can have any shape that is easy for a user to grip between the fingers and can include, for example, a D-ring style handle as shown in FIG. 2. The turnkey 16 is capable of rotating 360° and pivoting 90°.

The locking member 20 shown in FIGS. 1 and 2, is pivotally connected to the base 2 by a pair of hinges (not shown) mounted on opposite lateral sides of the base 2. The locking member 20 serves to lock the winch 42 in position when the desired level of pressure on the appendage is achieved. The locking member 20 also serves as a means for locking the strap 12 in place on the tourniquet. The locking member 20 is formed with a ring portion at one end and a locking lever 22 at an opposite end. The locking lever 22 is operatively connected to, such as being snap fit onto, a lateral shaft on the second end 6 of the base 2 so that the locking lever 22 of the locking member 20 can be clasped and unclasped from the second end 6 of the base 2 as shown in FIG. 1. A free end 18 of the strap 12 can be threaded through the ring portion of the locking member 20, folded back over the strap 12, and pulled to tightly and securely position the strap 12 on the appendage. The strap 12 can then be locked into place on the tourniquet by pivoting the locking lever 22 downward.

A protective accordion-style bellows 14, shown in FIG. 1, covers the sliding platen 24, cord 28, posts 26a, 26b and winch 42 of the power system 8. The bellows 14 are flexible and capable of expanding and contracting in at least the longitudinal direction of the tourniquet based on the sliding movement of the platen 24. The bellows 14 can be formed from a polymeric material such as neoprene.

As shown in FIG. 2, the strap 12 is connected to the power system 8 and turnkey 16. The strap 12 can be a cinch strap approximately 1 to 2½ inches wide, and 30 inches or more in length. The strap can be made of, for example only, nylon or any suitable polymeric material, and have ribbing on at least one side to help secure the strap in place against the power system 8. The free end 18 of the strap 12 can include a feeder or gripping portion help the user attain a firm grasp on the strap 12. Heating a nylon strap to the point where the fibers are fused together can form the gripping portion.

One example of a method of restricting the flow of blood through or from an injured appendage, according to the first embodiment of the present invention includes: placing the base 2 on the appendage and encircling the appendage with the strap 12; threading the free end 18 of the strap 12 through the locking member ring and pulling down slowly and firmly until the strap 12 is secured tightly onto the appendage; pivoting the locking lever 22 downwardly over the free end 18 of the strap 12 to lock the strap in place; pivoting the turnkey 16, to an upright position so as to be vertical with respect to the base 2, and turning the turnkey 16 clockwise to thereby pull the cord 28 into tension between the platen 24 and the winch 42, until the turnkey 16, and therefore the winch 42 can no longer be turned. As a result, pressure on the appendage is increased. The turnkey 16 can then be pivoted to a horizontal position. Folding the locking member 20 over the winch 42 prevents the winch 42 from accidentally rotating.

One example of releasing pressure on the appendage or removing the tourniquet includes: loosening the cord 28 in the power system 8 by lifting the locking member 20 which will result in disengagement of the winch, then pivoting the turnkey 16 from a horizontal position to an upright position so as to be vertical with respect to the base; turning the turnkey 16 in a counterclockwise direction to rotate the underlying winch 42 in the reverse direction to release the tension between the platen 24 and the winch 42, and thereby pressure on the appendage; sliding the free end 18 of the strap 12 toward the locking member ring. As a result, the tourniquet 10 can be adjusted on or removed from the appendage. The tourniquet of the present invention is reusable in that it can be removed, loosened, and reapplied.

Figure 3:
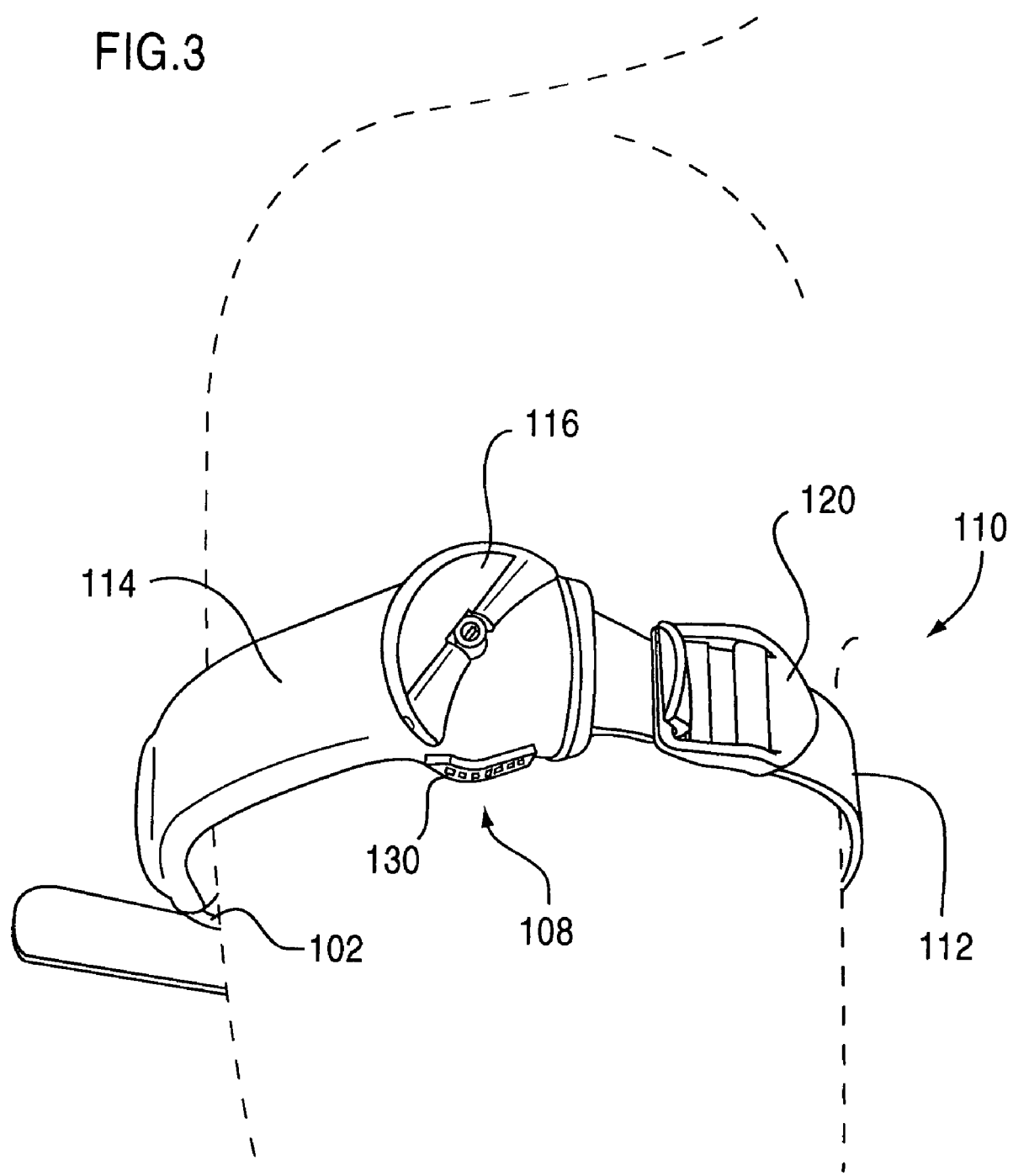
FIG. 3 illustrates a top perspective view of the tourniquet according to a second embodiment of the present invention, as applied to an appendage.

FIGS. 3-6 illustrate the mechanical advantage tourniquet 110 according to a second embodiment of the present invention, which includes components designed to apply a controlled pressure to the injured appendage and thereby restrict the flow of blood through or from the injury. As disclosed above, the mechanical advantage is a device that can multiply an output force while reducing an input force needed to create the output force. FIG. 3 illustrates the mechanical advantage tourniquet 110 as it can be applied to an injured appendage. The tourniquet 110 includes an arcuate member or C-clip 102 on which is mounted a mechanical advantage power system 108 having a tightening turnkey 116 for activating the mechanical advantage, and a release button 130 for canceling the mechanical advantage, a strap 112, and a locking member 120.

A shroud 114, shown in FIG. 3, is a sleeve-like member that extends circumferentially around an outer surface of the C-clip 102 and acts as a barrier to prevent foreign elements entering the power system 108. The shroud 114 can be diametrically cut such that the inside portion is shorter than the outside portion, lending an arcuate shape to the body of the shroud. The shroud or cover 114 is disposed over a portion of the mechanical advantage power system 108 leaving the tightening turnkey 116 exposed. Additional mechanical advantage components are disposed underneath the shroud 114, and will be discussed below.

The mechanical advantage power system 108 creates a mechanical advantage-assisted tension that cuts off the blood supply to an appendage once the strap 112 encircling the appendage has been pulled tight and locked into place by the locking member 120. In combination, the strap 112, along with the mechanical advantage power system 108 mounted onto the C-clip 102, serve as tightening means for tightening the tourniquet on the injured appendage.

As shown in FIG. 3, the C-clip 102 is placed onto the appendage. The strap 112 extends from a rear end portion of the C-clip 102, circumscribes the appendage, and fastens to a front end portion of the C-clip 102 with a locking member 120. The C-clip will now be discussed with reference to FIGS. 4-6.

Figure 4:
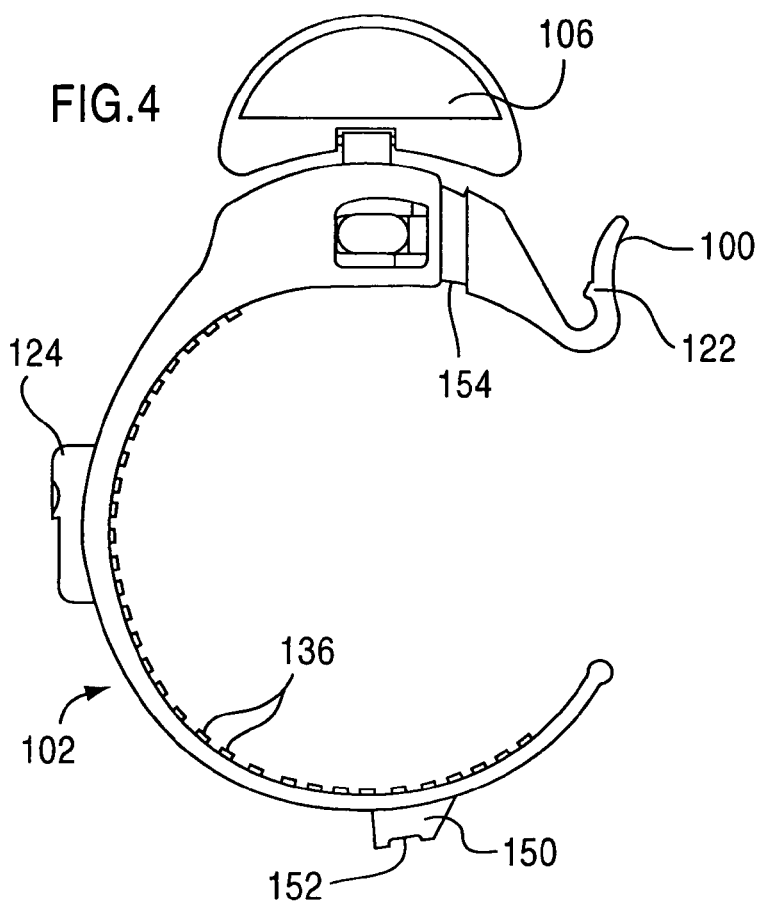
FIG. 4 illustrates a side view of the tourniquet C-clip member according to a second embodiment of the present invention.
Figure 5:
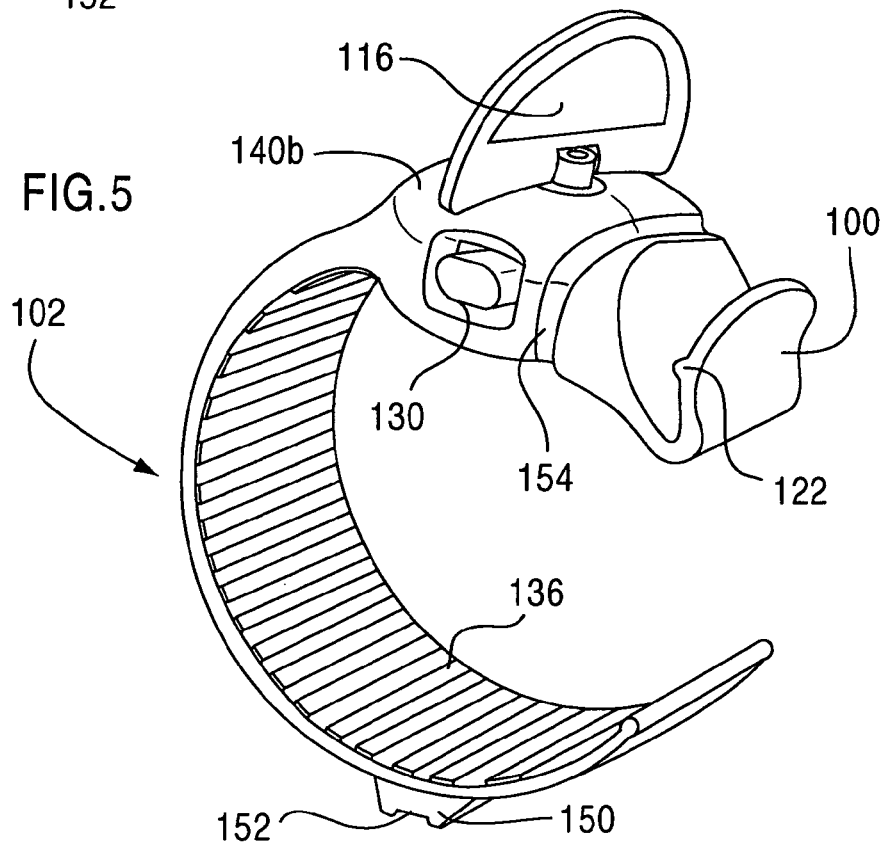
FIG. 5 illustrates a front perspective view of the tourniquet C-clip member according to a second embodiment of the present invention.

FIG. 4 illustrates a side view of the C-clip 102 according to a second embodiment of the present invention. The C-clip 102 is the innermost portion of the mechanical advantage tourniquet 110 and directly contacts the appendage or body part in which the flow of blood is to be restricted. As such, the C-clip 102 serves as a mounting means for mounting the tourniquet 110 onto the injured appendage. The C-clip is flexible and can be made by any means, including for example, injection molding a polymeric material. The polymeric material can include, but is not limited to acetal, nylon, polypropylene, and polyethylene. As such, the C-clip can be made from a material having an elastic memory so that the C-clip can circumferentially open and then return to its original state. Due to its flexibility and elasticity, the C-clip can to fit various sizes of appendages. As shown in FIGS. 4 and 5, the C-clip includes a hook 100 with detent 122 at the front end of the C-clip 102. The hook 100 of the C-clip is flared so as to relieve hot spotting during construction. The C-clip 102 also has protrusions 136 forming a crenellated inner surface for gripping the surface of appendage. A strap guide 150 is mounted along an outer surface of the C-clip 102 to guide the strap 112 from the rear end portion of the C-clip to a front end portion.

The tightening turnkey 116, shown in an upright position in FIGS. 4 and 5, is secured to a winch or cord retracting device 142. By turning the turnkey 116, the winch 142 rotates and pulls a winding cord that extends from the platen 124 to the winch 142 into tension, thereby providing a mechanical advantage for tightening the tourniquet 110 on the appendage. The turnkey 116 folds down for compact storage and flips up for rotation in order to tighten or loosen the tourniquet 110. The turnkey 116 can have a half-moon or semicircular shape, or any other shape that allows the user to easily grasp and rotate the turnkey. Further, the turnkey 116 can include a ribbed or textured surface to prevent the user's fingers from slipping off of the turnkey during use.

Figure 6:
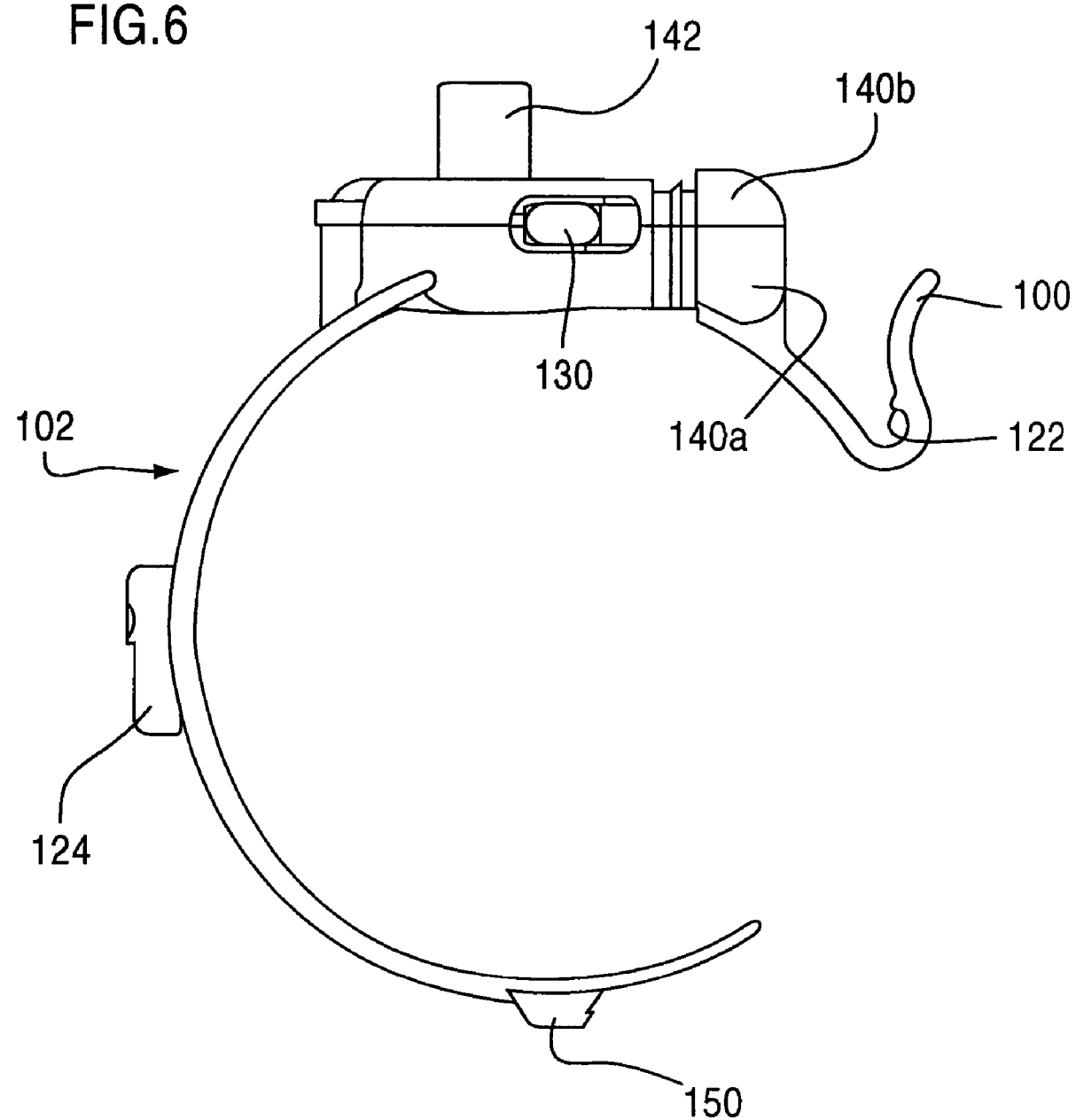
FIG. 6 illustrates a side view of the tourniquet C-clip member and integral mechanical advantage power system and attached platen according to a second embodiment of the present invention.

FIG. 6 illustrates a side view of the C-clip 102 according to the second embodiment of the present invention. The mechanical advantage power system 108 includes the platen 124, release button 130 and winch 142, which are shown mounted onto the C-clip 102. The winch 142 and release button 130 are disposed in a housing 140a formed integrally with the C-clip at the front end. The housing 140a has a housing cover 140b.

Figure 7:
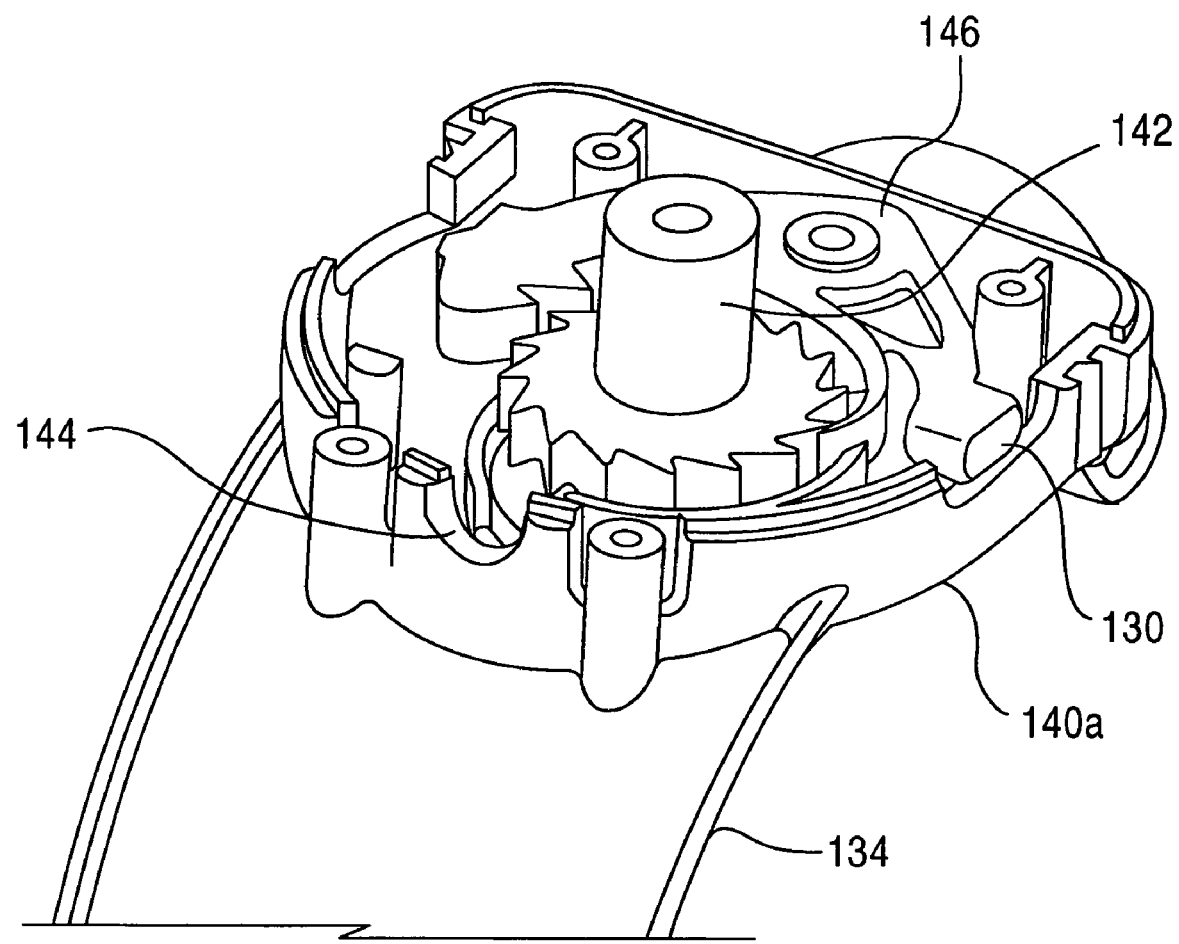
FIG. 7 illustrates an exemplary interior view of a mechanical advantage power system housing according to a second embodiment of the present invention.

An exemplary view of the interior of the housing 140a including components of the power system 108 is shown in FIG. 7. The power system 108 within the housing 140a includes a windlass arrangement comprising the winch 142 and pawl 146. The winch 142 serves to tighten the overall tourniquet on the appendage. The winch prevents over-winding, cord tangling and breakage that can occur with a tightening pulley system. The winch 142 includes a plurality of angled teeth that engage the pawl 146, which rests tangentially over the teeth. The pawl 146 permits rotation of the winch 142 in one direction only. Thus, when the turnkey 116 is rotated, the winch 142 rotates in a predetermined direction allowing the pawl 146 to slide over the teeth. The pawl 146 catches the teeth of the winch 142 if the winch attempts to rotate in the reverse direction.

Figure 11:
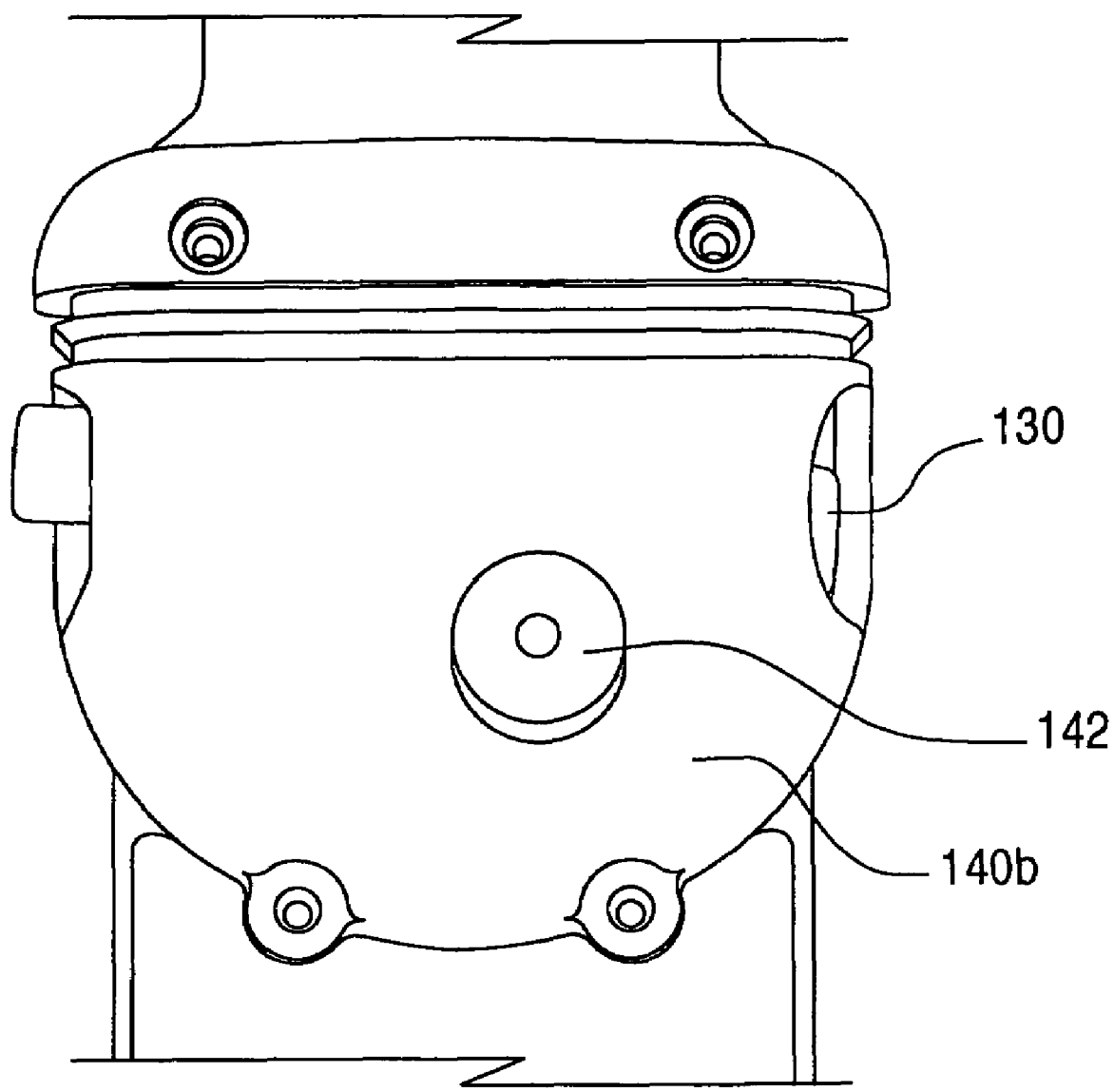

In order to loosen the cord 128 in the power system 108, and thereby reduce the pressure on the appendage, the user can press or slide the release button 130, which removes the pawl 146 from engagement with the teeth of the winch 142. Thus, when the winch rotates in the reverse direction, the pawl 146 does not catch the winch teeth. FIG. 11 illustrates the button as extending from the housing 140a, 140b indicating that the pawl 146 is engaged with the winch 142 to provide the mechanical advantage for tightening the tourniquet.

Figure 8:
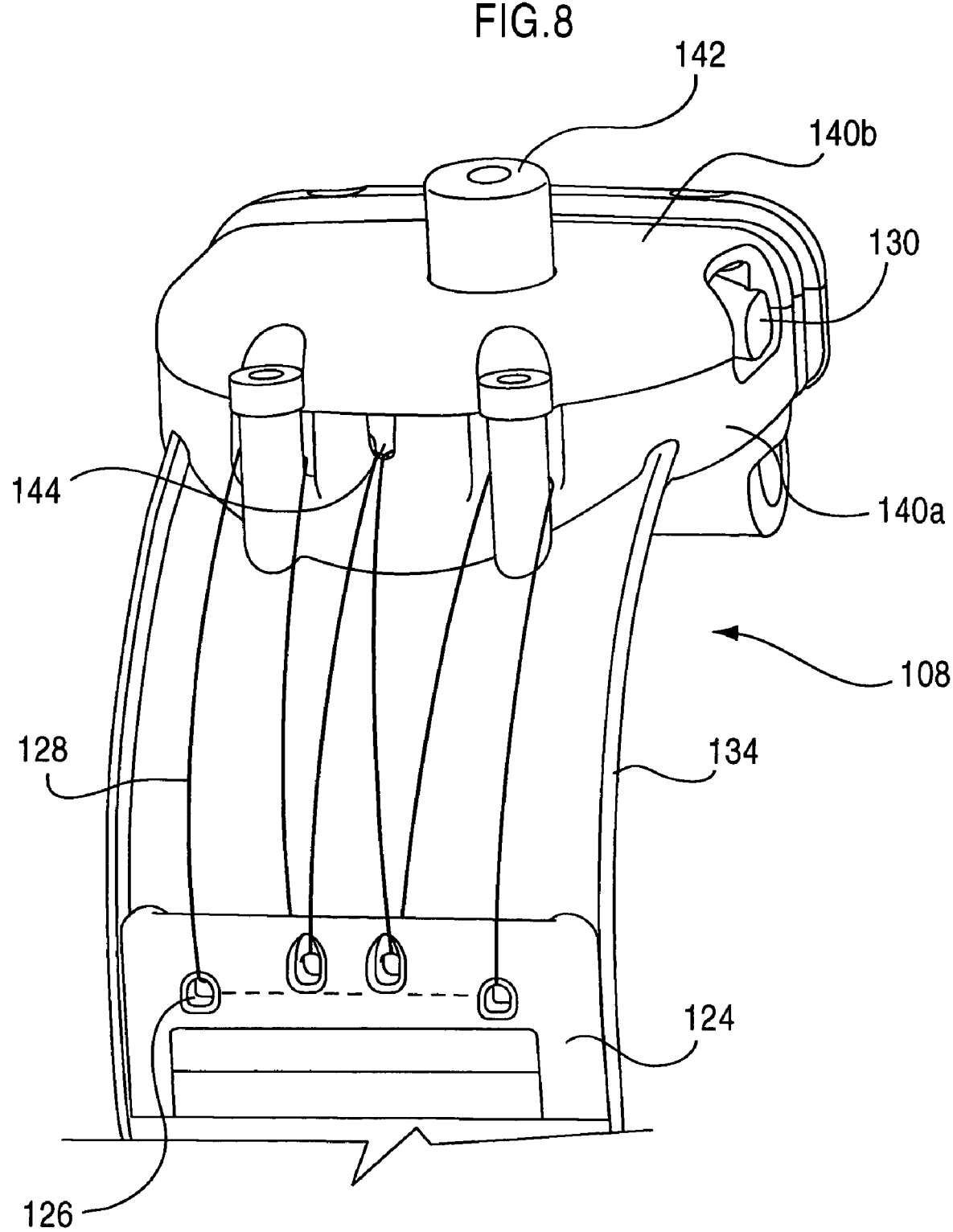
FIG. 8 illustrates an exemplary top-rear perspective view of the mechanical advantage power system components on the tourniquet C-clip member according to a second embodiment of the present invention.
Figure 9:
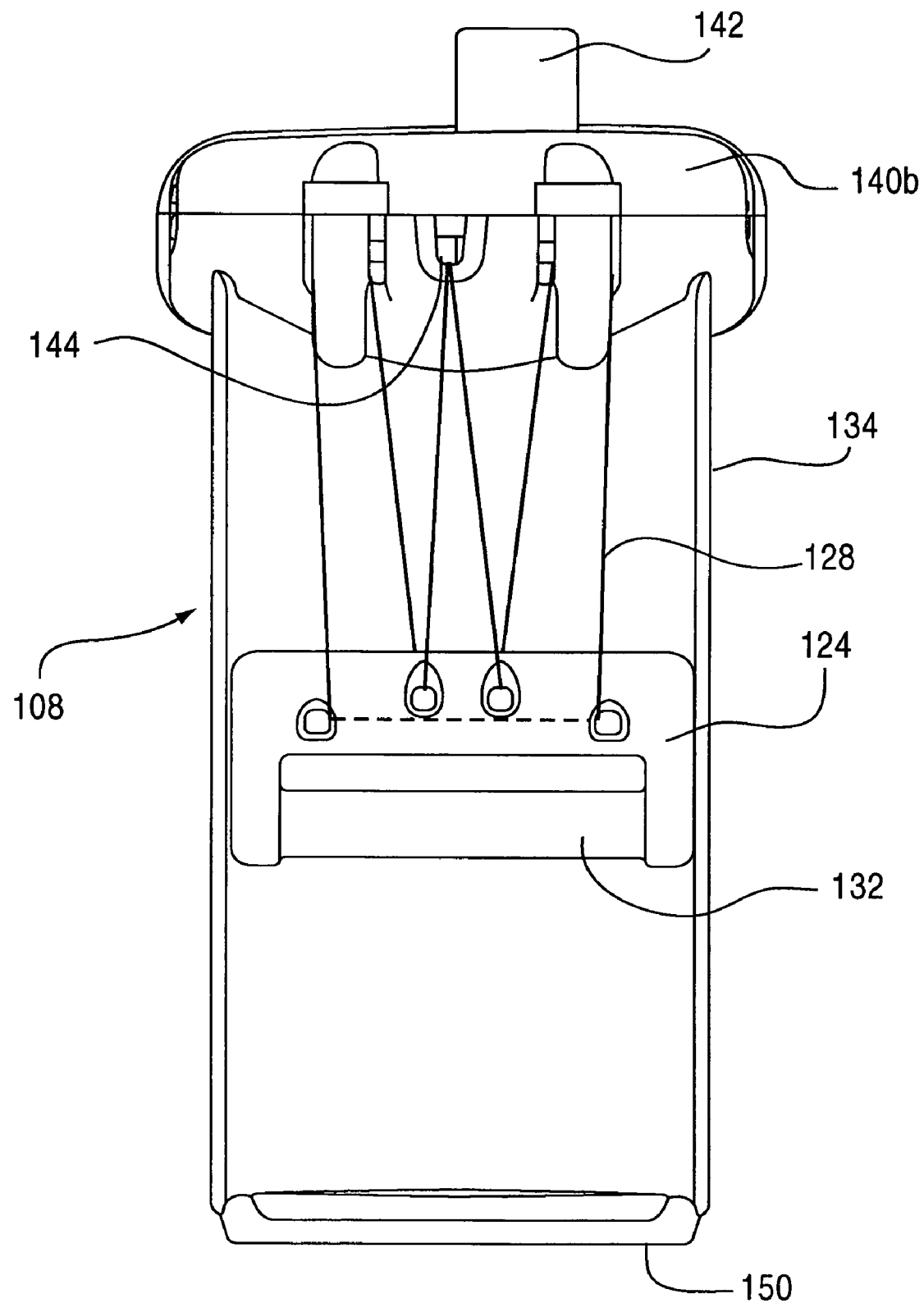
FIG. 9 illustrates an exemplary rear view of the mechanical advantage power system components on the C-clip member of the tourniquet according to a second embodiment of the present invention.

FIGS. 8 and 9 illustrate components of the power system 108 along a rear end portion of the C-clip 102. These components include an integrated, graduated track 134 formed on an outer surface of the C-clip 102 to allow a platen 124 mounted on the track 134 at a rear surface of the C-clip 102, to slide thereon. The platen 124 can be formed from any polymeric material including but not limited to nylon and acetal. The platen 124 includes a cross bar 132, as seen in FIG. 9, for mounting the strap 112 to the rear end portion of the C-clip 102, and a plurality of apertures 126 through which a pair of interwoven or braided cords 128, tied together, are threaded. The cords 128 of the present invention are low in friction and can be a polyester blend, having a high strength-to-weight diameter ratio. The cord 128 is threaded from the platen 124 to a pair of bosses mounted on the C-clip adjacent to the housing 140a, 140b. The bosses serve to mount the housing cover 140b onto the housing 140a. The cord 128 is routed in a serpentine manner between the platen 124, bosses and winch 142 in the housing. The cord 128 enters the housing through an opening 144 and is wrapped around the body of the winch 142 when the winch is rotated. The housing cover 140b prevents the cord 128 from migrating or sliding off of the winch 142.

When disposed on the C-clip 102, the shroud 114 is elastically fixed at one end to a groove 152 in the strap guide and at the other end in a groove 154 between the housing 140a, 140b and the hook 100.

To close the tourniquet 110, the strap 112, is pulled around the C-clip 102 through the strap guide 150 to the hook 100, which is disposed on the front end of the C-clip 102. The locking member 120 is attached to the end of the strap 112 and is operatively connected to the hook 100. The strap 112 tightens the entire mechanical advantage tourniquet 110 onto and around the appendage. The strap 112 can be approximately 1 to 2½ inches wide, and 30 inches or more in length so that the tourniquet is long enough use on all bodily appendages of different sized individuals.

By fastening the locking member 120 with the hook 100, the ends of the C-clip 102 are joined, closing the mechanical advantage tourniquet. The locking member 120 can include any well-known or currently sold ladder-style buckle such as that used for backpacks. Thus, the locking member 120 allows the strap to be adjusted on the appendage without having to unhook the strap 112 from the hook 100. The locking member 120 serves as locking means for locking the strap in place on the appendage.

The release button 130 includes a push-in detent molded into the shroud 114, which has a fail-safe return to the original position. The release button 130 can be positioned to minimally protrude from the side of the housing 140a so as to reduce accidental release of the winch 142

Figure 10:
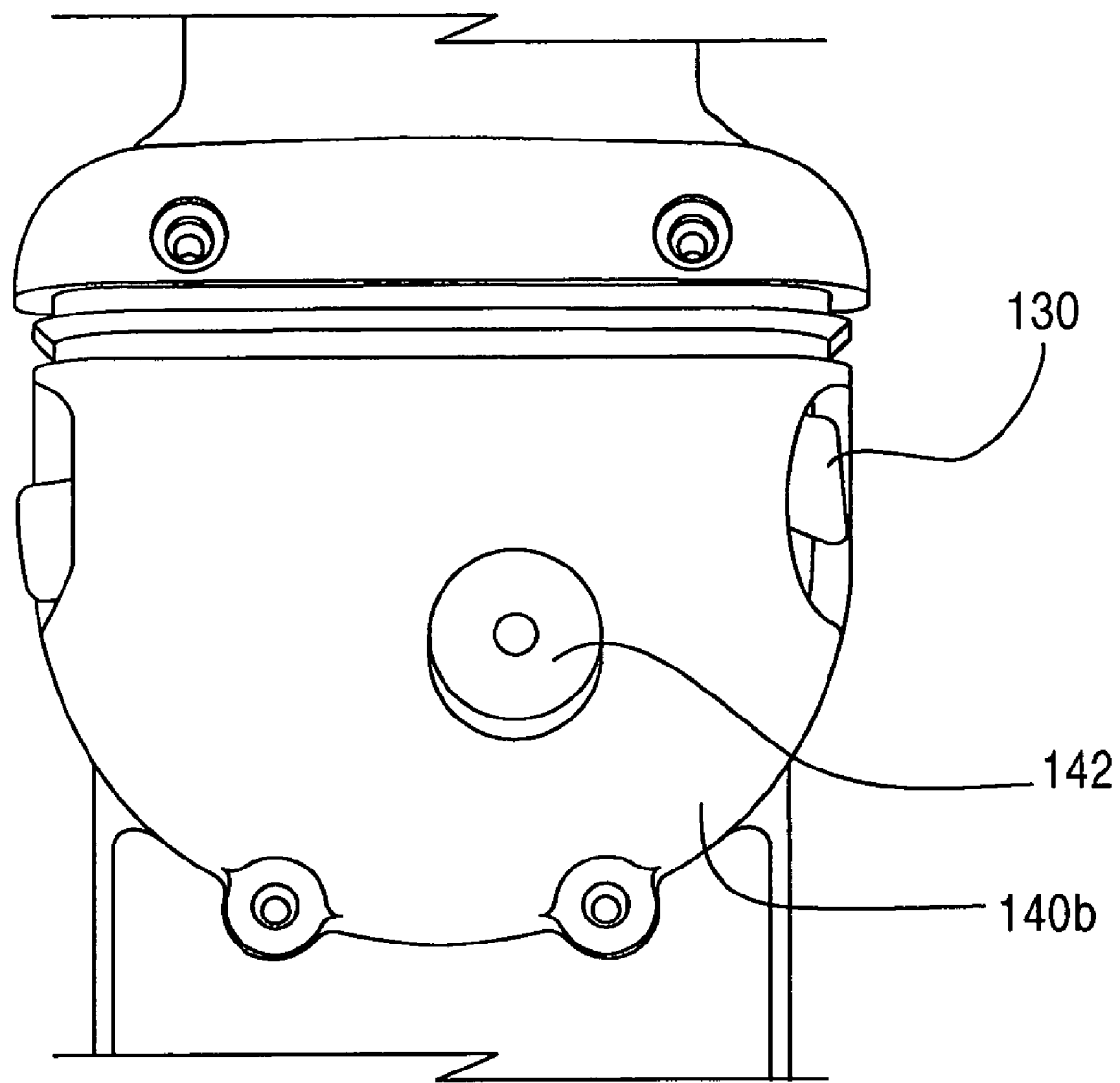
FIGS. 10 and 11 illustrate an exemplary top view of the housing and release button of the mechanical advantage power system according to a second embodiment of the present invention.

FIG. 10 illustrates an exemplary top view of the housing cover 140b and release button 130 according to a second embodiment of the present invention. The release button 130 is illustrated as protruding from the housing, indicating that the pawl is engaged with the winch 142.

FIG. 11 illustrates the button 130 as depressed or slid in the direction of the platen, indicating that the pawl has been released from the winch 142 so that the tourniquet can be loosened.

Figure 12:
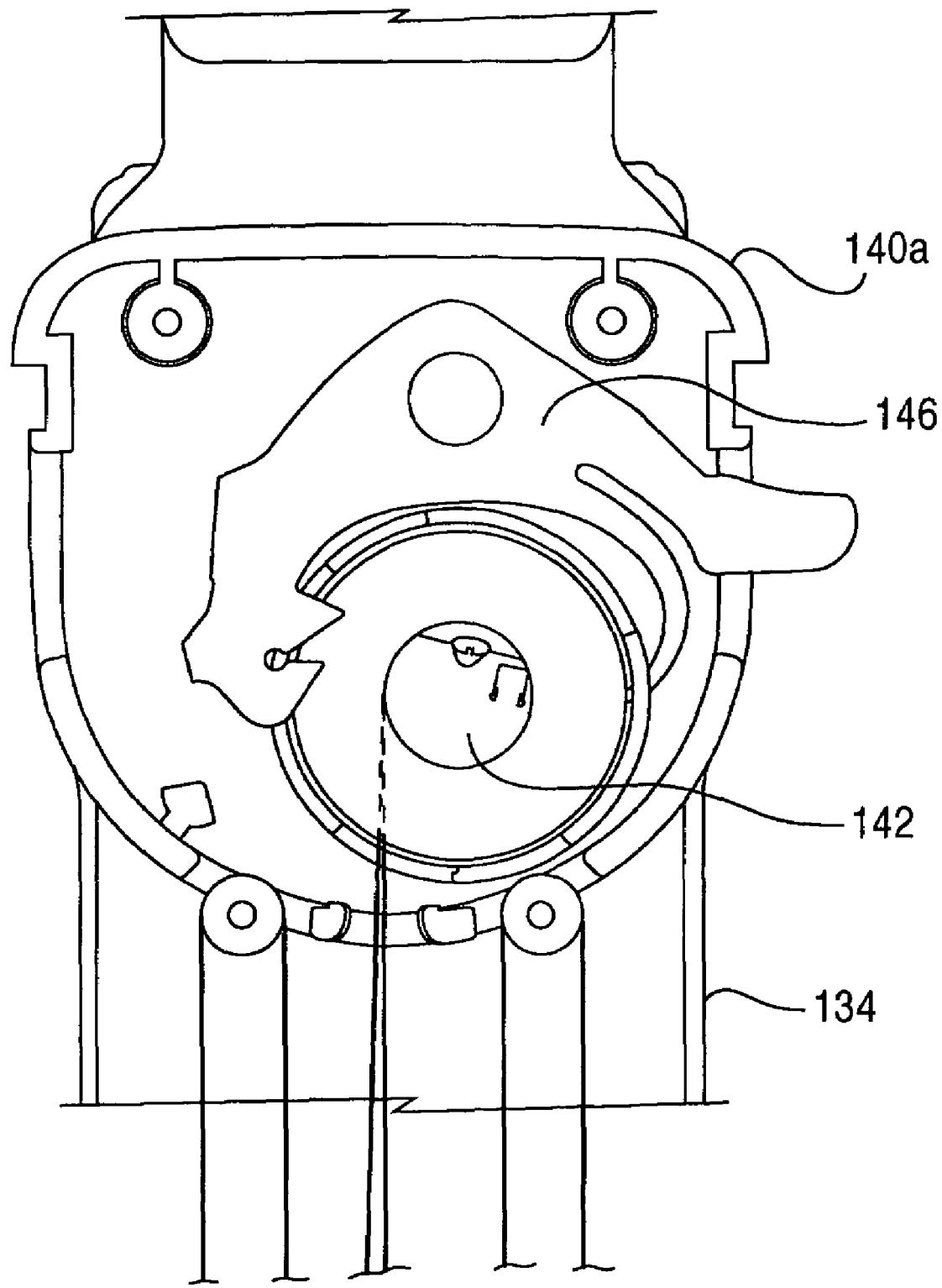
FIG. 12 illustrates an exemplary winch and engaged pawl arrangement of the mechanical advantage power system according to a second embodiment of the present invention.
Figure 13:
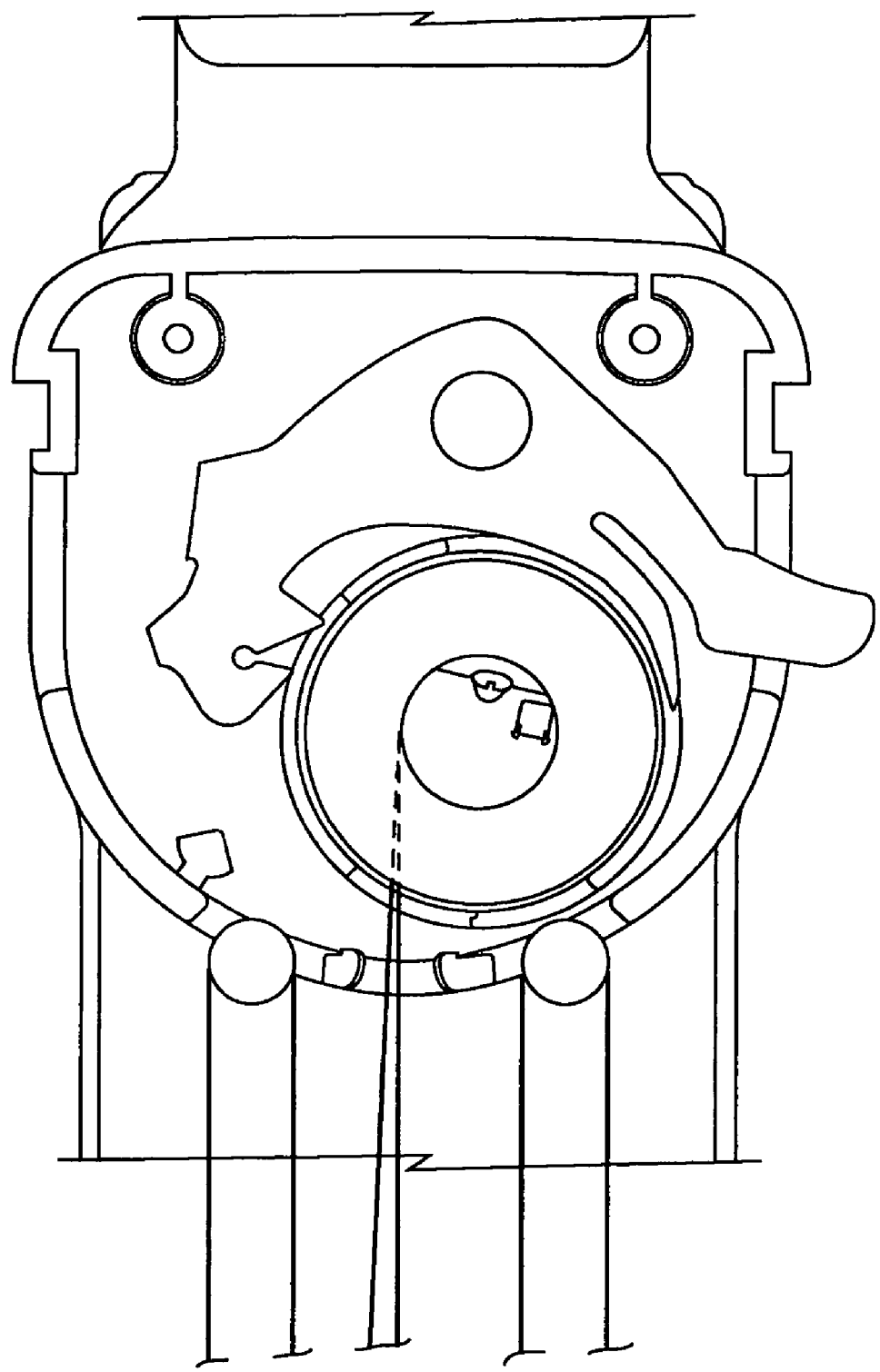
FIG. 13 illustrates an exemplary winch and released pawl arrangement of the mechanical advantage power system according to a second embodiment of the present invention.

FIG. 12 illustrates another exemplary view of the pawl 146 engaged with the winch 142, while FIG. 13 illustrates a further exemplary view of the pawl 146 released from the winch 142.

An example of a method of restricting the flow of blood through a body part according to the second embodiment of the present invention includes: placing the C-clip 102 and the elongated strap 112 around the appendage; engaging the locking member 120 device with the first end or hook 100 of the C-clip 102; pulling the strap 112 in a direction tangent to the surface of the C-clip 102, until the strap is secured tightly to the body part; raising the turnkey from a folded or horizontal position to a vertical position so that it is perpendicular to the plane of the shroud and C-clip; turning the turnkey in a predetermined direction until the turnkey and thus the winch 142 can no longer be turned indicating that maximum pressure is being applied to the appendage; and folding the turnkey to a horizontal position.

The method for changing or releasing the pressure on the appendage includes pressing the release button to release the pawl 146 from engagement with the winch 142; turning the turnkey 116 in the opposite direction; and loosening the strap 112 and locking member 120 while the locking member is engaged with the hook 100 or loosening the strap 112 upon removing the locking member 120 from hook 100 to release pressure on the appendage. Pulling an intermediate portion of the strap in a direction opposite to a tightening direction further loosens the tourniquet from the appendage.

The tourniquet 10, 110 is weather resistant in that the neoprene bellows or shroud is designed to prevent foreign substances or debris from entering the power system. The neoprene bellows and shroud also slow the amount of water that can enter the power system and thereby allow the tourniquet to resist sinking in water. The tourniquet can be any color suitable for use. For example, the tourniquet can be colored in a camouflage pattern such as for example, beige and brown to match military uniforms used in a desert environment; or black, olive and green to match military uniforms used in a jungle or forested environment. The tourniquet can also have, at least in part, colors suitable for Emergency Medical Technician or Emergency Medical Services use such as, for example, fluorescent orange or fluorescent yellow. In addition, the overall tourniquet or any one of the components can be coated with a luminescent paint to facilitate night vision.

Example embodiments of the present invention have now been described in accordance with the above advantages. It will be appreciated that these examples are merely illustrative of the invention. Many variations and modifications will be apparent to those skilled in the art.

We claim:

1. A pressure control apparatus for restricting a flow of blood through or from a body part, the apparatus comprising:
   a member for mounting on the body part, the member having a first end and a second end;
   a primary tightening device mounted on the member for adjusting a pressure of the apparatus on the body part, wherein the primary tightening device comprises:
      a retracting device;
      a platen slidably mounted on the member between the first end of the member and the retracting device;
      at least one elongated flexible element extending from the retracting device around at least one engaging element on the platen to provide a mechanical advantage whereby, on operation of the retracting device to retract the flexible element, the platen is drawn along the member; and
      a handle coupled to operate the retracting device to retract the flexible element;
   and wherein the apparatus further comprises a secondary tightening device coupled between the platen and the member and configured for circumferentially tightening the apparatus around the body part.

2. The pressure control apparatus according to claim 1, wherein the secondary tightening device comprises a strap.

3. The pressure control apparatus according to claim 1 wherein the member comprises a resiliently flexible C-clip.

4. The pressure control apparatus according to claim 3, wherein the second end of the member comprises a hook and the secondary tightening device comprises a buckle for coupling with the hook.

5. A tourniquet for restricting a flow of blood through or from an appendage, the tourniquet comprising:
   a base mountable on the appendage, the base having a first end and a second end;
   a mechanical advantage power system mounted on the base for controlling a pressure of the tourniquet on the appendage, the power system comprising:
      a windlass;
      a platen slidably mounted on the base;
      at least one flexible element extending between the windlass and the platen, the at least one flexible element passing around at least one engaging element on the platen to provide a mechanical advantage upon retraction of the flexible element by the windlass;
      a strap having a first end coupled to the platen for circumferentially tightening the tourniquet on the appendage; and
      a coupling connecting a second end of the strap to the base to close the tourniquet around the appendage;
   whereby, upon operation of the windlass, the platen is pulled along the base, thereby tightening the tourniquet.

6. The tourniquet according to claim 5, wherein the windlass comprises a release mechanism for canceling the pressure of the tourniquet on the appendage.

7. The tourniquet of claim 5, wherein the base comprises a C-clip having material memory, the C-clip adapted to circumferentially open to accept the appendage therein and return toward an original state so as to be secured to the appendage.

8. The tourniquet of claim 5, wherein the windlass comprises a rotatable winch wherein the flexible element is wrapped around the winch and pulled into tension upon rotation of the winch.

9. The tourniquet of claim 8, further including:
   a pawl to engage the winch and prevent the winch from rotating in a direction so as to loosen the flexible element; and a release button configured to disengage the pawl from the winch.

10. A pressure control apparatus for applying pressure to a body part, the pressure control apparatus comprising:
    a base for positioning the apparatus on the body part; the base having a first end and second end; and
    a mechanical advantage power system mounted on the base, the system including a rotatable retracting device positioned on the base and a member slidably positioned on the base;
    a flexible element connecting the retracting device and the slidable member, the flexible element extending around at least one engaging element of the slidable member to provide a mechanical advantage; and
    a rotating means for rotating the retracting device to pull the flexible element into tension by wrapping the flexible element around the retracting device and thereby pull the slidable member along the base to tighten the apparatus.

11. A tourniquet, comprising:
    a C-clip having a first end and a second end, the C-clip having material memory to circumferentially open to accept an appendage therein and return to its original state so to be held in place on the appendage;
    a windlass mounted on the C-clip, the windlass configured to tighten the tourniquet to apply pressure to the appendage;
    a platen slidably mounted on the C-clip between the first end of the C-clip and the windlass;
    at least one flexible element connecting the platen and the windlass, wherein the at least one flexible element extends around at least one engaging element of the platen to provide a mechanical advantage;
    a strap having a first end coupled to the platen and a second end coupled to the C-clip,
    whereby the platen is pulled along the C-clip toward the windlass upon operation of the windlass to tighten the tourniquet.

12. The tourniquet of claim 11, wherein the windlass comprises a rotatable winch wherein the flexible element is wrapped around the winch and pulled into tension upon rotation of the winch.

13. The tourniquet of claim 12, further including:
    a pawl arranged to engage the winch to lock the winch against releasing tension on the flexible element; and
    a release button configured to disengage the pawl from the winch.

14. A tourniquet comprising:
    a base comprising a first end and a second end;
    a platen slidable along the base;
    a strap comprising a first end coupled to the platen and a second end coupled to the base;
    a tightening mechanism mounted on the base, the tightening mechanism comprising:
       a windlass;
       at least one flexible element extending from the windlass to an anchor point, the at least one flexible element passing around at least one engaging element of the platen to provide a mechanical advantage upon operating the windlass to pull the platen along the base to tighten the tourniquet.

15. A tourniquet according to claim 14, wherein the at least one flexible element passes around a least one engaging element fixed relative to the windlass after passing around the at least one engaging element of the platen.

16. A tourniquet according to claim 15, wherein the engaging elements are selected from the group consisting of posts, apertures and bosses.

17. A tourniquet according to claim 14, wherein the at least one flexible element comprises two lengths of flexible element each extending from the windlass to a respective anchor point and each passing around at least one respective engaging element of the platen.

18. A tourniquet according to claim 17, wherein first and second ones of the two lengths of flexible element are arranged in mirror-image symmetry.

19. A tourniquet according to claim 14, wherein the tightening mechanism is fixed to the base.

20. A tourniquet according to claim 14, wherein an axis of rotation of the windlass is substantially perpendicular to the base.

21. A tourniquet according to claim 14, wherein the windlass comprises a rotatable winch.

22. A tourniquet according to claim 21, wherein the windlass comprises a pawl arranged to engage the winch to hold the flexible element in tension.

23. A tourniquet according to claim 22, comprising a release mechanism configured to disengage the pawl from the winch.

24. A tourniquet according to claim 21, comprising a turnkey coupled to rotate the winch.

25. A tourniquet according to claim 24, wherein the turnkey is pivotable between an upright position and a folded position, wherein the turnkey is operable in the upright position.

26. A tourniquet according to claim 14, comprising a locking mechanism releasably coupling the second end of the base to the second end of the strap.

27. A tourniquet according to claim 26, wherein the locking mechanism comprises a locking lever pivotally attached to the second end of the base.

28. A tourniquet according to claim 14, wherein the base comprises a C-clip having an elastic memory, wherein the C-clip is resiliently deformable to receive and hold an appendage therein.

29. A tourniquet according to claim 28, wherein the C-clip comprises a strap guide between the platen and the first end of the base.

30. A tourniquet according to claim 29, wherein the second end of the base comprises a hook and the second end of the strap is configured for coupling with the hook.

31. A tourniquet according to claim 14, wherein the base comprises one or more tracks for guiding sliding movement of the platen along the base.

* * * * *